(12) United States Patent
Shie

(10) Patent No.: US 12,280,210 B2
(45) Date of Patent: Apr. 22, 2025

(54) BITE DEVICE AND AUXILIARY MEMBER THEREOF

(71) Applicant: Chang-Bih Shie, Tainan (TW)

(72) Inventor: Chang-Bih Shie, Tainan (TW)

( * ) Notice: Subject to any disclaimer, the term of this patent is extended or adjusted under 35 U.S.C. 154(b) by 36 days.

(21) Appl. No.: 18/261,788

(22) PCT Filed: Jan. 25, 2022

(86) PCT No.: PCT/IB2022/050618
§ 371 (c)(1),
(2) Date: Jul. 17, 2023

(87) PCT Pub. No.: WO2022/162520
PCT Pub. Date: Aug. 4, 2022

(65) Prior Publication Data
US 2024/0100279 A1 Mar. 28, 2024

(30) Foreign Application Priority Data
Jan. 26, 2021 (TW) .................................. 110102883

(51) Int. Cl.
*A61M 16/04* (2006.01)
*A61B 1/24* (2006.01)

(52) U.S. Cl.
CPC ........... *A61M 16/0493* (2014.02); *A61B 1/24* (2013.01)

(58) Field of Classification Search
CPC ........... A61M 16/0488–0497; A61M 16/0465; A61M 2025/022; A61B 1/24;
(Continued)

(56) References Cited

U.S. PATENT DOCUMENTS

| 2006/0272647 A1* | 12/2006 | Hauge | A61M 16/0493 |
| | | | 128/207.14 |
| 2014/0196722 A1* | 7/2014 | Sethiya | A61M 16/0434 |
| | | | 128/207.14 |
| 2019/0125213 A1* | 5/2019 | Rockwell | A61B 5/097 |

FOREIGN PATENT DOCUMENTS

| CN | 101227946 A | 7/2008 |
| JP | 2001190675 A * | 7/2001 |

(Continued)

OTHER PUBLICATIONS

English Machine Translation of JP-2001190675-A provided by PE2E (Year: 2001).*

(Continued)

*Primary Examiner* — Joseph D. Boecker
*Assistant Examiner* — Brian T Khong
(74) *Attorney, Agent, or Firm* — Rosenberg, Klein & Lee

(57) ABSTRACT

A bite device is configured to be placed in the mouth (92) of a patient, facilitates insertion of soft tubes (91) from the outside into the mouth (92) of the patient, and includes a bite member (2) and an auxiliary member (3). The bite member (2) includes an abutment portion (21), a biting portion (216) extending outwardly from one side of the abutment portion (21), a sleeve portion (22) opposite to the biting portion (216), and a central hole (23) for insertion of one soft tube (91) therethrough. The auxiliary member (3) includes a fixing plate structure (31) having a main auxiliary hole (317) removably sleeved on the sleeve portion (22), and at least one secondary auxiliary hole (318) for insertion of another soft tube (91) into the mouth (92) of the patient.

7 Claims, 11 Drawing Sheets

(58) Field of Classification Search
CPC . A61J 15/0061; Y10S 128/26; Y10S 128/911; A62B 9/06
See application file for complete search history.

(56) References Cited

FOREIGN PATENT DOCUMENTS

| TW | 201420142 A | * | 6/2014 | |
|---|---|---|---|---|
| WO | 2006132940 A1 | | 12/2006 | |
| WO | WO-2016129285 A1 | * | 8/2016 | ............ A61M 16/04 |

OTHER PUBLICATIONS

English Machine Translation of TW-201420142-A provided by PE2E (Year: 2014).*
English Machine Translation of WO-2016129285-A1 provided by PE2E (Year: 2016).*
First Office Action in a Corresponding Taiwan Application Dated Jan. 10, 2022.
Second Office Action in a Corresponding Taiwan Application Dated Jun. 21, 2022.
Notice of Allowance in a Corresponding Taiwan Application Dated Apr. 24, 2023.
Third Office Action in a Corresponding Taiwan Application Dated Nov. 22, 2022.

* cited by examiner

BITE DEVICE AND AUXILIARY MEMBER THEREOF

FIELD

The disclosure relates to a bite device and an auxiliary member thereof.

BACKGROUND

Referring to FIGS. 1 and 2, generally, when a soft tube 10 (e.g., a sputum suction tube) needs to be inserted into an oral cavity of a patient, a bite member 11 is first placed in the mouth 901 of the patient. The bite member 11 defines a centerline (T) extending in a front-rear direction, and has an abutment portion 111, a biting portion 112 extending rearwardly from and having a width narrower than that of the abutment portion 111, a protruding portion 113 extending forwardly from the abutment portion 111 and opposite to the biting portion 112, and a central hole 114 extending through the biting portion 112, the abutment portion 111 and the protruding portion 113 along the centerline (T). The abutment portion 111 has an outer peripheral surface 115 that is circular and that surrounds the centerline (T).

In use, the bite member 11 is first placed in the mouth 901 of the patient with a rear surface of the abutment portion 111 abutting against the lips 902 of the patient and the protruding portion 113 extending out of the mouth 901 of the patient, after which the soft tube 10 is inserted into the oral cavity of the patient through the central hole 114.

However, when the patient must be inserted with multiple soft tubes 10, 10' (e.g., an endotracheal tube for a respirator, a gastroscope, etc.), each of the soft tubes 10' can only be inserted into the mouth 901 of the patient through a space between the abutment portion 111 and one side of the lips 902 of the patient, so that the soft tubes 10' can only abut or press against both sides of the lips 902 of the patient. As a result, not only the lips 902 of the patient are directly pressed by the weight of the soft tubes 10', the soft tubes 10' also cannot be easily and stably inserted into the mouth 901 of the patient, so that it is necessary to use and fix a large amount of gauze strips and tapes on the cheeks of the patient, thereby causing discomfort to the patient.

SUMMARY

Therefore, an object of the present disclosure is to provide an auxiliary member of a bite device that can alleviate at least one of the drawbacks of the prior art.

According to this disclosure, an auxiliary member of a bite device is configured for removable connection with a bite member thereof. The bite member is configured to be placed in the mouth of a patient and facilitates insertion of a plurality of soft tubes from the outside into the mouth of the patient. The bite member defines a centerline and includes an abutment portion, a biting portion extending outwardly from one side of the abutment portion and configured to be located in the mouth of the patient, a sleeve portion extending outwardly from the other side of the abutment portion and opposite to the biting portion along the centerline, and a central hole that extends through the biting portion, the abutment portion and the sleeve portion and that is suitable for insertion of one of the soft tubes therethrough.

The auxiliary member includes a fixing plate structure configured to be removably sleeved on the sleeve portion of the bite member and having a first side surface for facing the abutment portion of the bite member, a second side surface opposite to the first side surface, and a main auxiliary hole and at least one secondary auxiliary hole extending through the first side surface and the second side surface. The main auxiliary hole is configured to be sleeved on the sleeve portion of the bite member. The at least one secondary auxiliary hole is configured for insertion of another one of the soft tubes into the mouth of the patient.

Another object of this disclosure is to provide a bite device that can alleviate at least one of the drawbacks of the prior art.

According to this disclosure, a bite device is configured to be placed in the mouth of a patient, facilitates insertion of a plurality of soft tubes from the outside into the mouth of the patient, and includes a bite member and an auxiliary member. The bite member defines a centerline and includes an abutment portion, a biting portion extending outwardly from one side of the abutment portion and configured to be located in the mouth of the patient, a sleeve portion extending outwardly from the other side of the abutment portion and opposite to the biting portion along the centerline, and a central hole that extends through the biting portion, the abutment portion and the sleeve portion and that is suitable for insertion of one of the soft tubes therethrough. The auxiliary member includes a fixing plate structure removably sleeved on the sleeve portion and having a first side surface facing the abutment portion, a second side surface opposite to the first side surface, and a main auxiliary hole and at least one secondary auxiliary hole extending through the first side surface and the second side surface. The main auxiliary hole is sleeved on the sleeve portion. The at least one secondary auxiliary hole is configured for insertion of another one of the soft tubes into the mouth of the patient.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
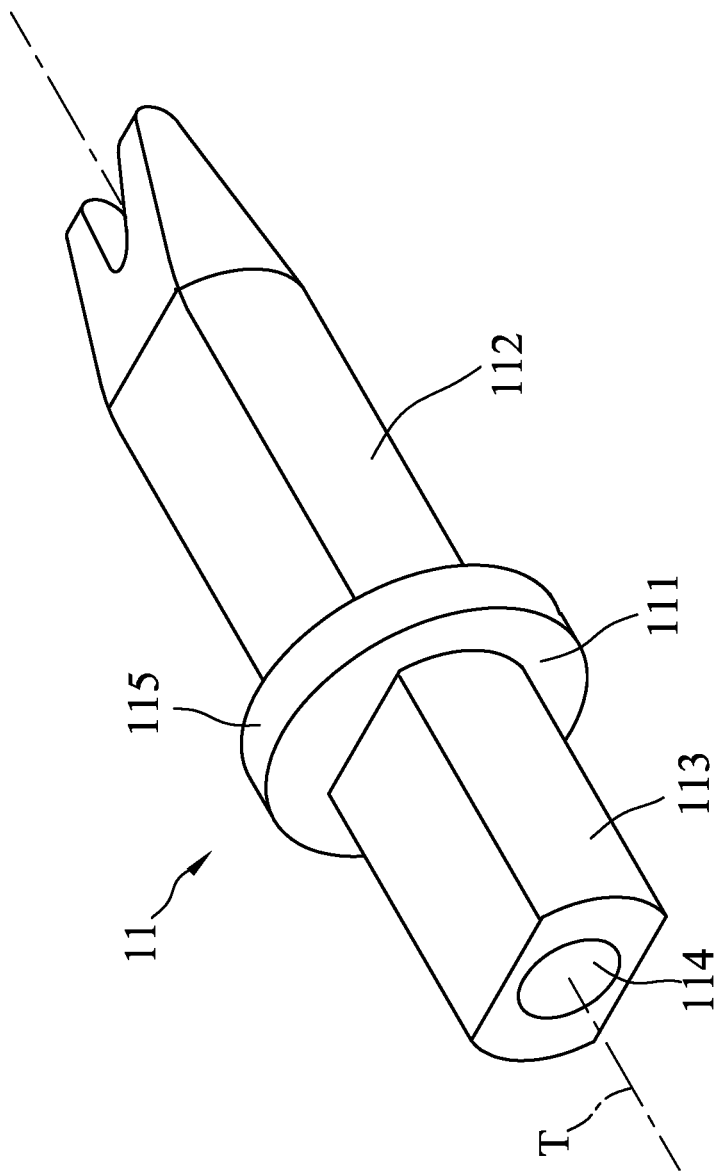
FIG. 1 is a perspective view of a conventional bite member.
Figure 2:
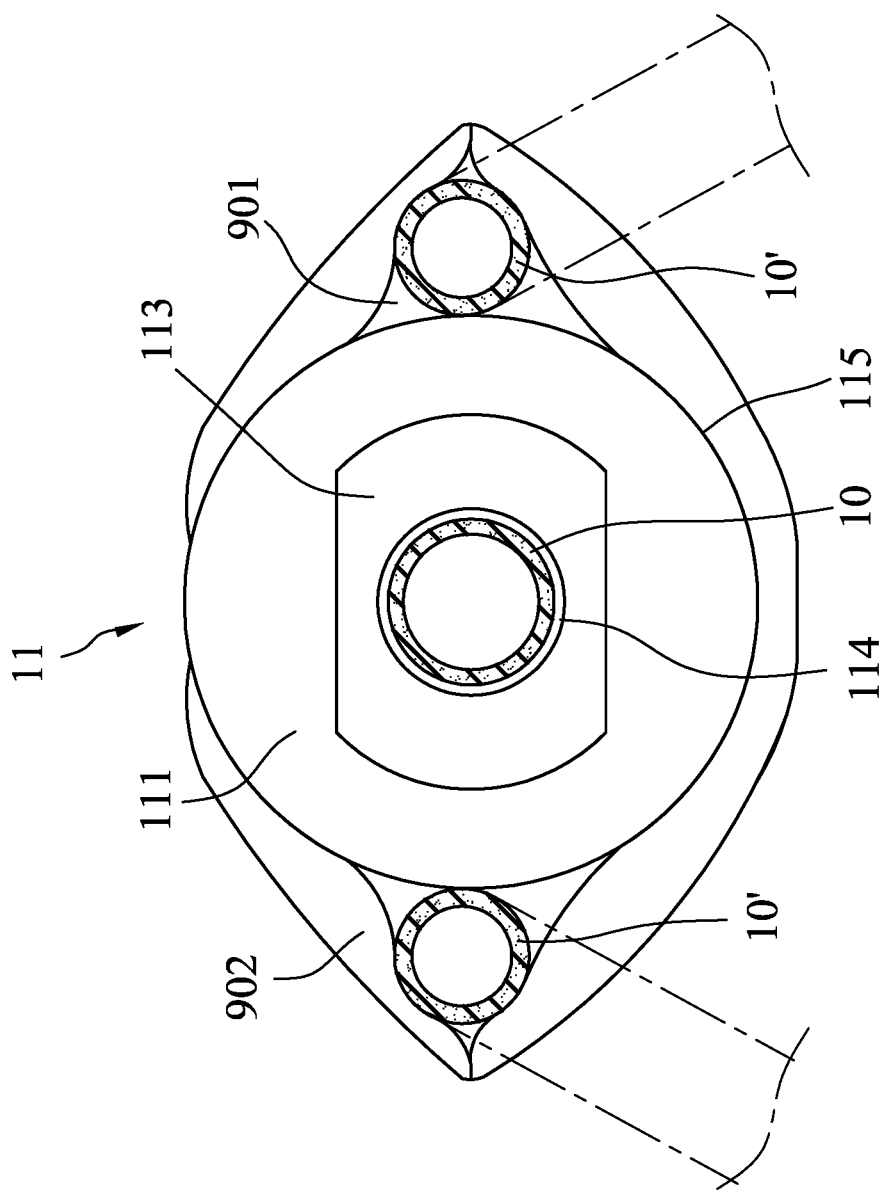
FIG. 2 is a partial sectional view of the conventional bite member in a state of use.

Before the present disclosure is described in greater detail with reference to the accompanying drawings and embodiments, it should be noted herein that like elements are denoted by the same reference numerals throughout the disclosure.

Figure 3:
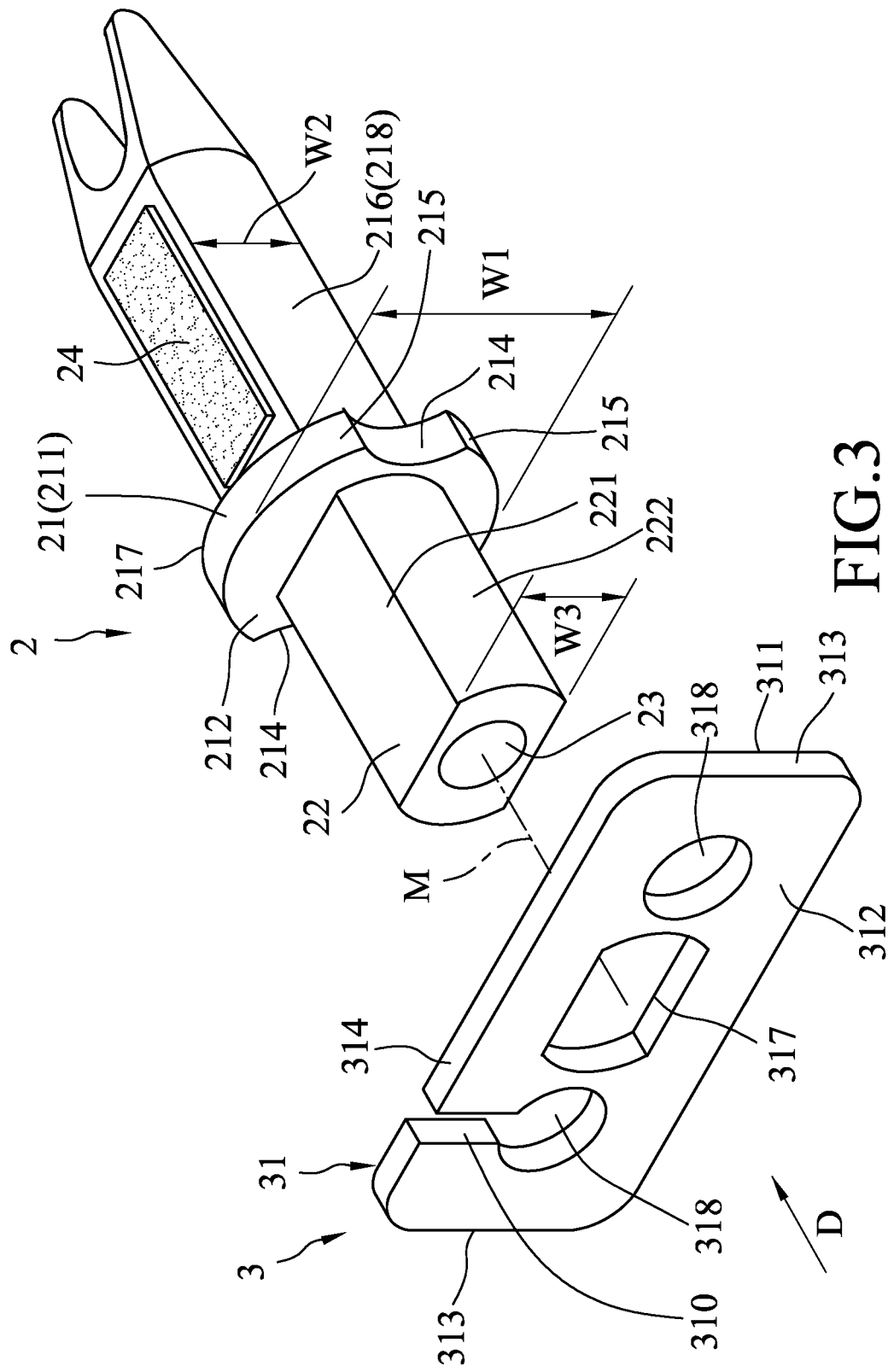
FIG. 3 is an exploded perspective view of a bite device according to the first embodiment of the present disclosure.
Figure 4:
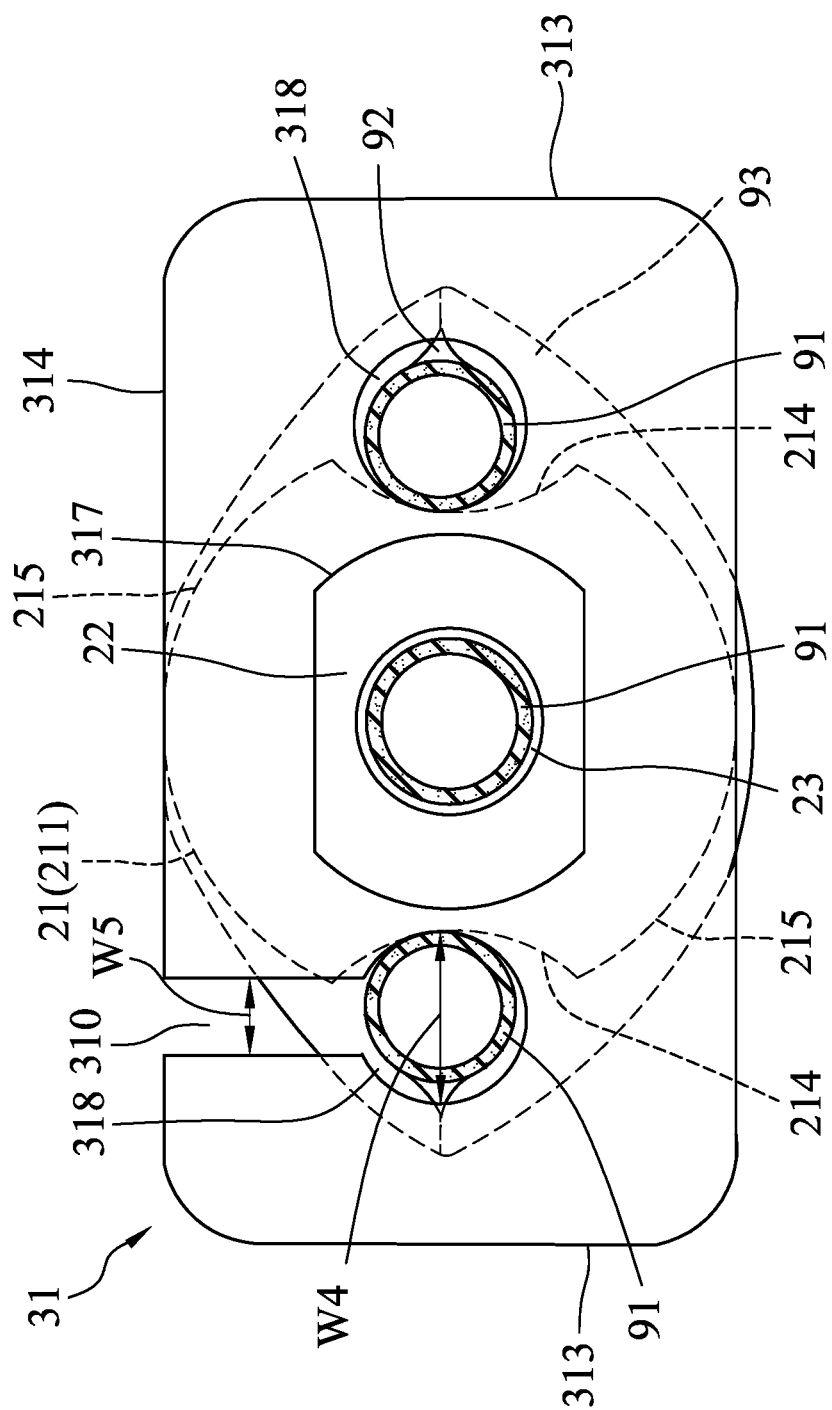
FIG. 4 is an assembled partial sectional view of the first embodiment in a state of use.
Figure 5:
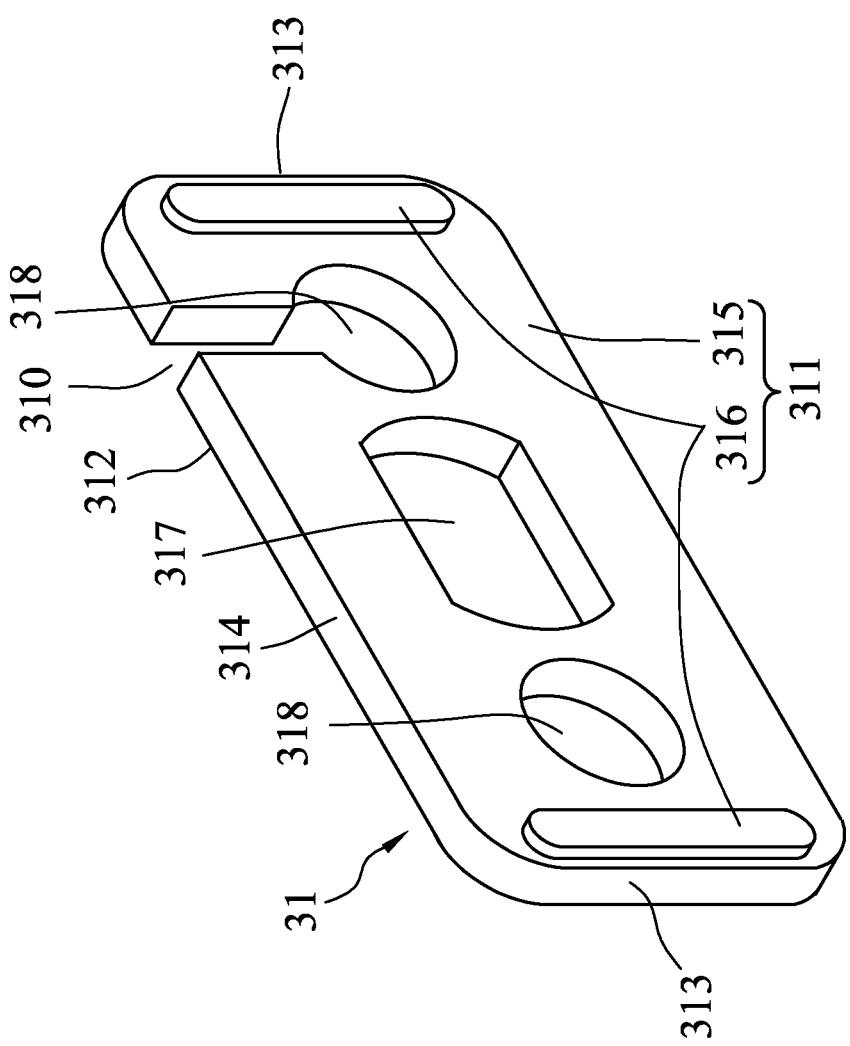
FIG. 5 is a perspective view of an auxiliary member of the first embodiment taken from another angle.

Referring to FIGS. 3 to 5, a bite device according to the first embodiment of the present disclosure is configured to be placed in the mouth 92 of a patient, facilitates insertion of a plurality of soft tubes 91 from the outside into the mouth 92 of the patient, and includes a bite member 2 and an auxiliary member 3.

The bite member 2 defines a centerline (M) extending in a front-rear direction, and includes an abutment portion 21, a biting portion 216, a sleeve portion 22, two contact portions 24 (only one is visible in FIG. 3), and a central hole 23 that extends through the biting portion 216, the abutment portion 21 and the sleeve portion 22 along the centerline (M) and that is suitable for insertion of one of the soft tubes 91 therethrough.

The abutment portion 21 has an outer peripheral surface 211 surrounding the centerline (M), a front abutment surface 212 connected to a front periphery of the outer peripheral surface 211 and configured to face away from the patient, and a rear abutment surface 217 opposite to the front abutment surface 212 along the centerline (M) and configured to face the patient. The outer peripheral surface 211 has two abutment areas 215 spaced apart in a top-bottom direction transverse to the centerline (M) and curving toward each other, and is formed with two cutouts 214 between the abutment areas 215 and opposite to each other in a left-right direction transverse to the centerline (M). In this embodiment, each cutout 214 has a concave surface, and the concave surfaces of the cutouts 214 face away from each other. Each cutout 214 serves as an auxiliary tube abutment area.

The biting portion 216 is configured to be placed in the mouth 92 of the patient, extends outwardly from the rear abutment surface 217 along the centerline (M), and an outer peripheral surface 218. The outer peripheral surface 211 of the abutment portion 21 has a width (W1) measured in the top-bottom direction larger than a width (W2) of the biting portion 216 measured in the top-bottom direction.

The sleeve portion 22 extends outwardly from the front abutment surface 212 along the centerline (M), and has a substantially rectangular cross section with two flat surfaces 221 spaced apart in the top-bottom direction and two curved surfaces 222 between the flat surfaces 221. The curved surfaces 222 curve away from each other. Further, the sleeve portion 22 has a width (W3) measured in the top-bottom direction smaller than the width (W1) of the outer peripheral surface 211 of the abutment portion 21.

The contact portions 24 are respectively disposed on top and bottom sides of the outer peripheral surface 218 of the biting portion 216. The contact portions 24 are made of elastic silicone material, and are suitable for contact with the teeth of the patient. In other variations of this embodiment, the contact portions 24 may be integrally connected as one piece surrounding the outer peripheral surface 218.

The auxiliary member 3 includes a fixing plate structure 31 removably sleeved on the sleeve portion 22 of the bite member 2. The fixing plate structure 31 has a rectangular shape, and has a first side surface 311 facing the front abutment surface 212 of the abutment portion 21, a second side surface 312 opposite to the first side surface 311, two third side surfaces 313 interconnecting left and right lateral ends of the first and second side surfaces 311, 312, and two fourth side surfaces 314, one of which interconnects top ends of the first and second side surfaces 311, 312 and top ends of the third side surfaces 313, and the other one of which interconnects bottom ends of the first and second side surfaces 311, 312 and bottom ends of the third side surfaces 313.

The fixing plate structure 31 is made of a silicone material and is molded in one piece. The first side surface 311 has a flat area 315, and two spaced-apart raised areas 316 protruding from left and right sides of the flat area 315 toward the front abutment surface 212. Each raised area 316 has the shape of an elongated strip, is proximate to a respective one of the third side surfaces 313, and extends in a same direction as the respective third side surface 313, that is, the top-bottom direction.

The fixing plate structure 31 further has a main auxiliary hole 317 extending through the first and second side surfaces 311, 312 along the centerline (M), and two secondary auxiliary holes 318 extending through the first and second side surfaces 311, 312 and located on left and right sides of the main auxiliary hole 317. The main auxiliary hole 317 has a substantially rectangular shape with two short sides that curve away from each other such that the contour thereof is similar to that of the sleeve portion 22 of the bite member 2. The main auxiliary hole 317 is sleeved on the sleeve portion 22 to prevent the fixing plate structure 31 from rotating relative to the sleeve portion 22 when the fixing plate structure 31 is sleeved on the sleeve portion 22.

Each secondary auxiliary hole 318 is located between the main auxiliary hole 317 and a corresponding one of the third side surfaces 313, and is spaced apart from a respective one of the raised areas 316. Further, each secondary auxiliary hole 318 corresponds in position to and aligns with a respective one of the cutouts 214 of the outer peripheral surface 211 of the abutment portion 21, and is not covered by the abutment areas 215 of the abutment portion 21. Each secondary auxiliary hole 318 is configured to allow insertion of a corresponding one of the soft tubes 91 therethrough. Each cutout 214 is configured for abutment of the corresponding soft tube 91 therewith after the latter passes through the corresponding secondary auxiliary hole 318.

In this embodiment, the fixing plate structure 31 further has a passage 310 extending from the fourth side surface 314 that interconnects the top ends of the first and second side surface 311, 312 to one of the secondary auxiliary holes 318, shown as a left one of the secondary auxiliary holes 318 in FIG. 3. The left secondary auxiliary hole 318 has a width (W4) larger than a width (W5) of the passage 10 measured in the left-right direction. The passage 10 is configured to allow a corresponding one of the soft tubes 91 to pass therethrough and enter the left secondary auxiliary hole 318, so that the corresponding one of the soft tubes 91 can be smoothly placed in the left secondary auxiliary hole 318. A right one of the secondary auxiliary holes 318 in FIG. 3 has a circular shape.

To use the bite device of this disclosure, the biting portion 216 of the bite member 2 is first placed in the mouth 92 of the patient such that the rear abutment surface 217 of the abutment portion 21 abuts against the lips 93 of the patient, after which the auxiliary member 3 is sleeved on the sleeve portion 22 of the bite member 2 through the main auxiliary hole 317 thereof until the first surface 311 of the fixing plate structure 31 abuts against and covers the front abutment surface 212 of the abutment portion 21. Next, three soft tubes 91 are respectively inserted into the mouth 92 of the patient through the central hole 23 in the bite member 2 and the secondary auxiliary holes 318 in the auxiliary member 3. At this time, the soft tubes 91 inserted into the secondary auxiliary holes 318 further abut against the concave surfaces of the cutouts 214 of the abutment portion 21 for carrying out measures, such as supplying of air, examination, suctioning of mucus, etc. When the diameter of a distal end of the soft tube 91 to be inserted into the mouth 92 of the patient is large (e.g., gastroscope), the large diameter soft tube 91 can be inserted through the passage 310 and into the left secondary auxiliary hole 318.

When there is no need for the bite device of this disclosure, the soft tubes 91 are first pulled out of the mouth 92 of the patient, after which the auxiliary member 3 and the bite member 2 are removed from the patient.

Through the cooperation of the fixing plate structure 31 of the auxiliary member 3 and the bite member 2, that is, with the secondary auxiliary holes 318 of the fixing plate structure 31 allowing insertion of corresponding soft tubes 91 therethrough so that the fixing plate structure 31 can support the soft tubes 91, and with the cutouts 214 of the outer peripheral surface 211 allowing abutment of the soft tubes 91 on the concave surfaces thereof, the soft tubes 91 can be stably inserted and positioned in the mouth 92 of the patient, so that use of many gauze strips and breathable tapes for securing the soft tubes 91 can be avoided. Further, the pressure on the lips 93 of the patient caused by the soft tubes 91 that are located on both sides of the mouth 92 of the patient can also be dispersed, thereby preventing the soft tubes 91 from only abutting against the lips 93 of the patient. Thus, the discomfort experienced by the patient during insertion of the soft tubes 91 can be reduced.

Moreover, by using the raised areas 316 at the first side surface 311 of the fixing plate structure 31, the first side surface 311 can be prevented from being attached to the cheeks of the patient, and friction between the auxiliary member 3 and the skin of the patient can also be minimized, thereby further reducing the discomfort caused by using the bite device of this disclosure for a long time.

Additionally, by reserving a space for the soft tubes 91 to pass through, when there is an urgent need to insert the soft tube 91, which is, for example, an endoscope, for performing hemostasis, blood drawing or examination of upper gastrointestinal bleeding of the patient, the soft tube or endoscope 91 can be inserted immediately through one of the secondary auxiliary holes 318 of the fixing plate structure 31 and the corresponding cutout 214 into the mouth 92 of the patient, so that use of the disclosure is relatively fast, simple and efficient, and there is no need to go through complicated processes of inserting and fixing the endoscope 91. Besides, the endoscope 91 can be inserted into the body of the patient from the mouth 92 thereof, rather than through the nostrils, so that situations, such as brain puncture injury, fracturing of the skull, and the risk of sinus infection, caused during insertion of the endoscope 91 can be avoided. Furthermore, the soft tube 91, which is, for another example, a nasogastric tube, can be held by the bite device of this disclosure, so that food can be fed through the mouth 92, and not the nose, of the patient.

It should be noted that the number of the secondary auxiliary hole 318 is not limited to two, and may be one in other variations of this embodiment. Further, in other variations of this embodiment, the fixing plate structure 31 may not be provided with the passage 310, or may be provided with two passages 310 that extend from the fourth side surface 314 thereof to the respective secondary auxiliary holes 318 depending on actual requirements.

Figure 6:
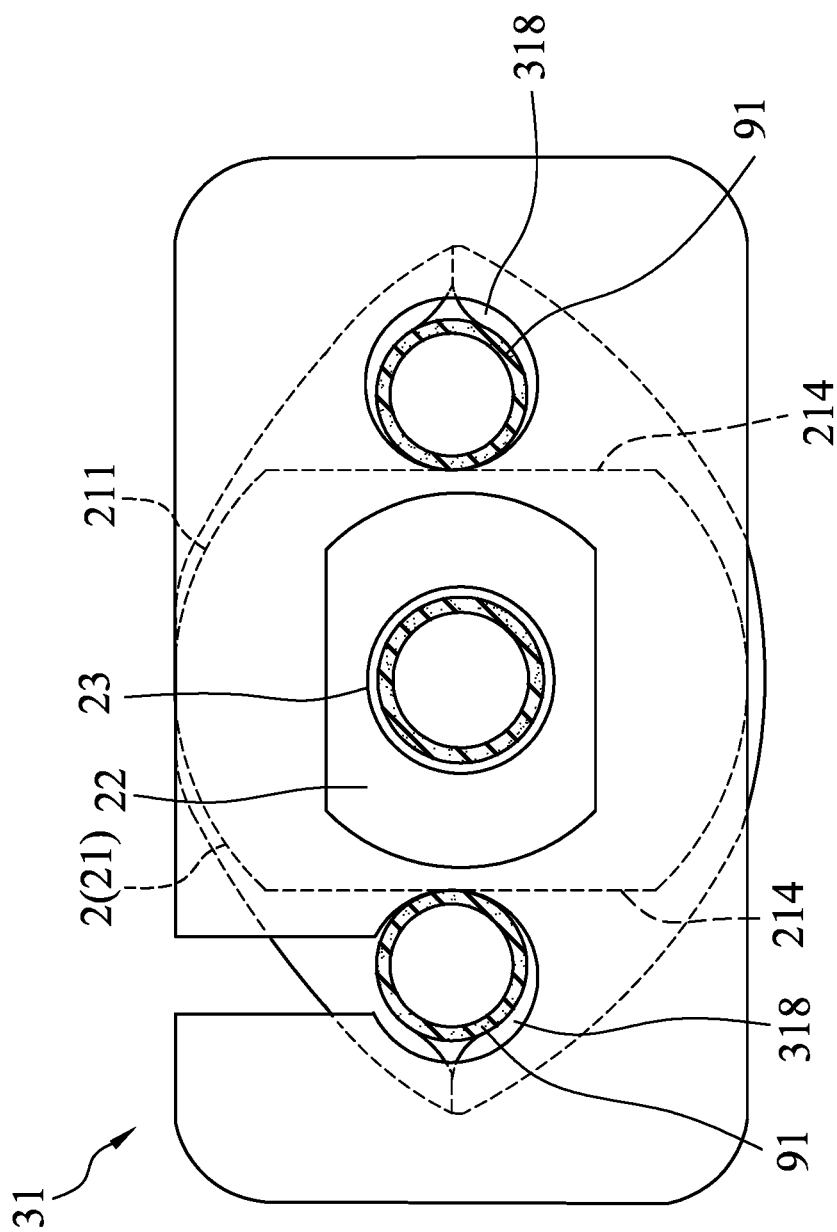
FIG. 6 is an assembled partial sectional view of a bite device according to the second embodiment of the present disclosure.

Referring to FIG. 6, the second embodiment of the bite device of this disclosure is identical to the first embodiment, and differs in that, in this embodiment, each cutout 214 of the outer peripheral surface 211 of the abutment portion 21 of the bite member 2 has a flat surface.

Figure 7:
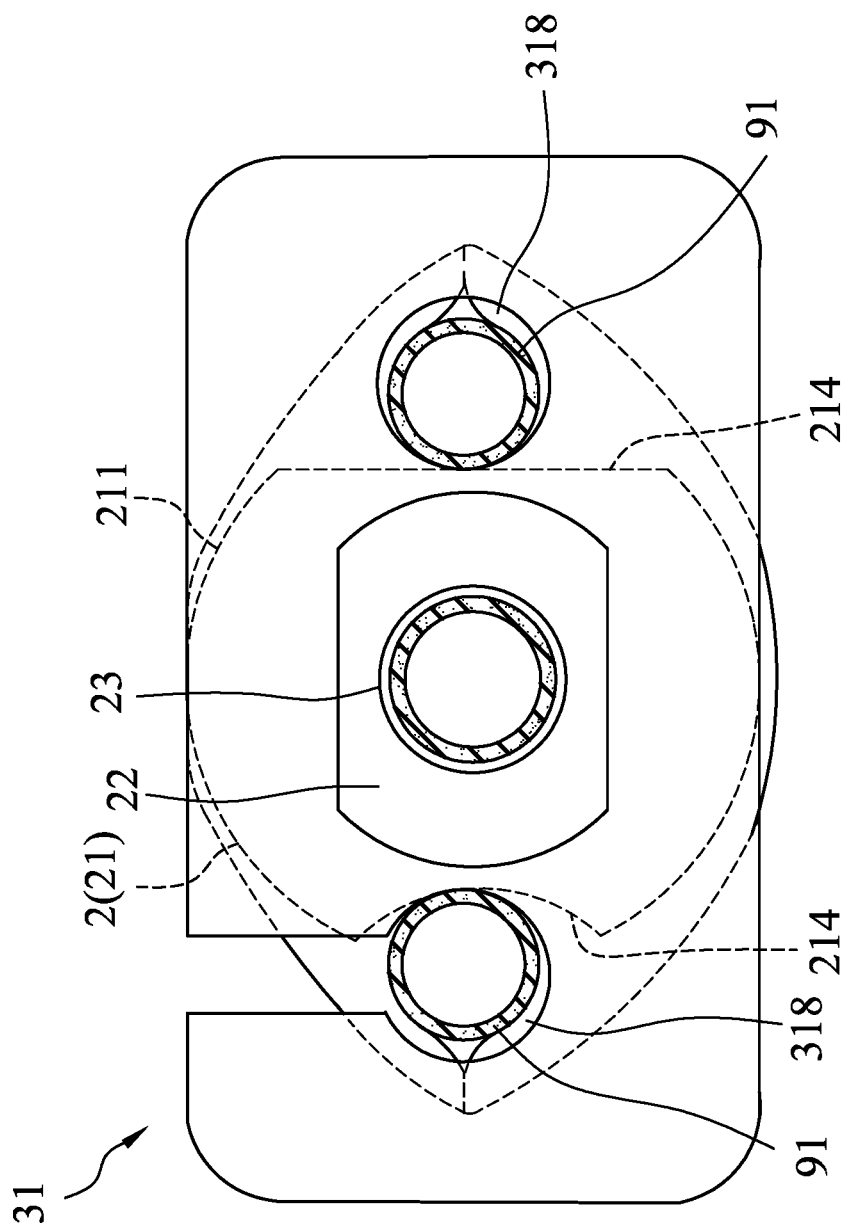
FIG. 7 is a view similar to FIG. 6, but illustrating an alternative form of the second embodiment.

FIG. 7 illustrates an alternative form of the second embodiment, in which one of the cutouts 214 has a concave surface, while the other cutout 214 has a flat surface.

Figure 8:
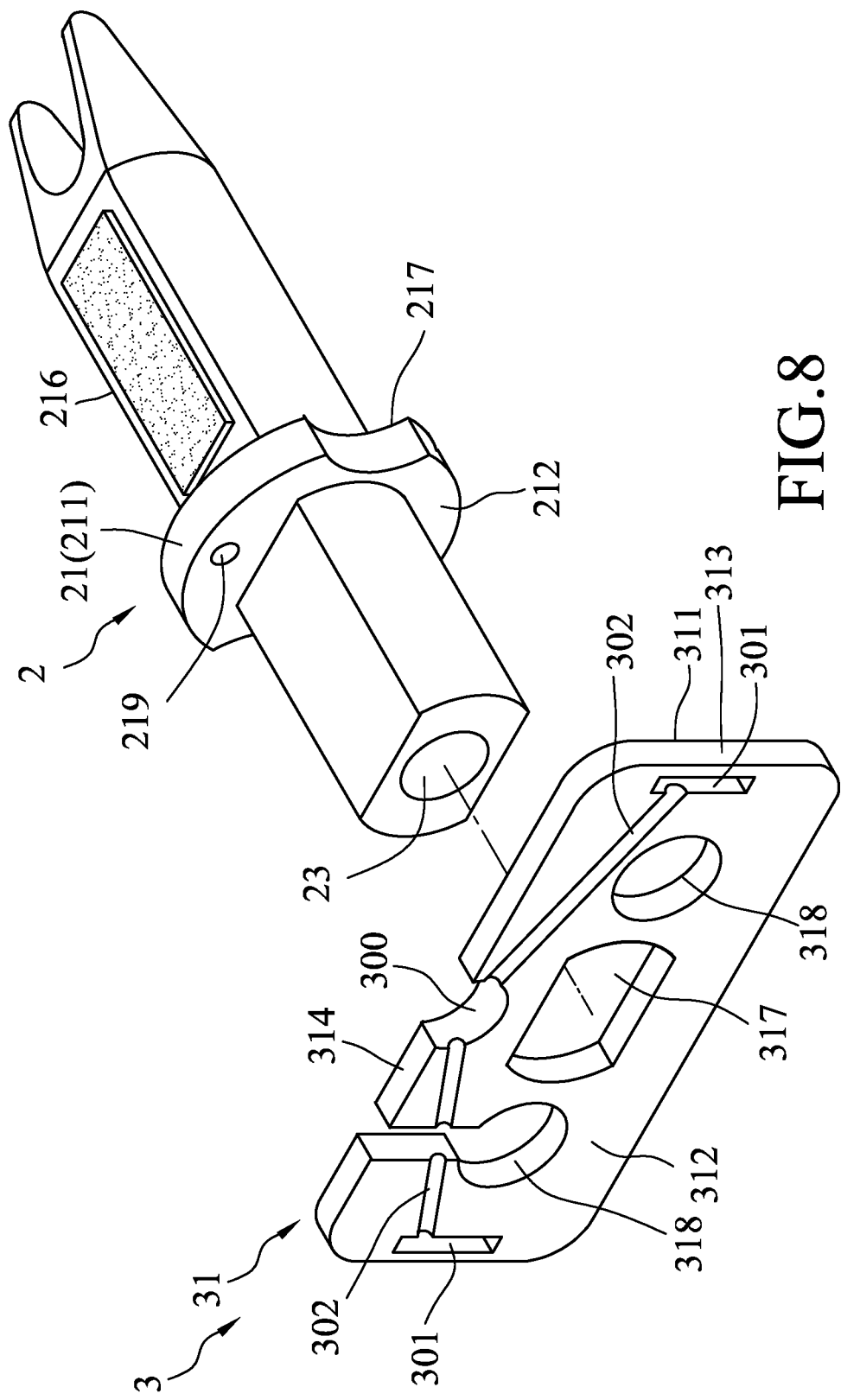
FIG. 8 is an exploded perspective view of a bite device according to the third embodiment of the present disclosure.
Figure 9:
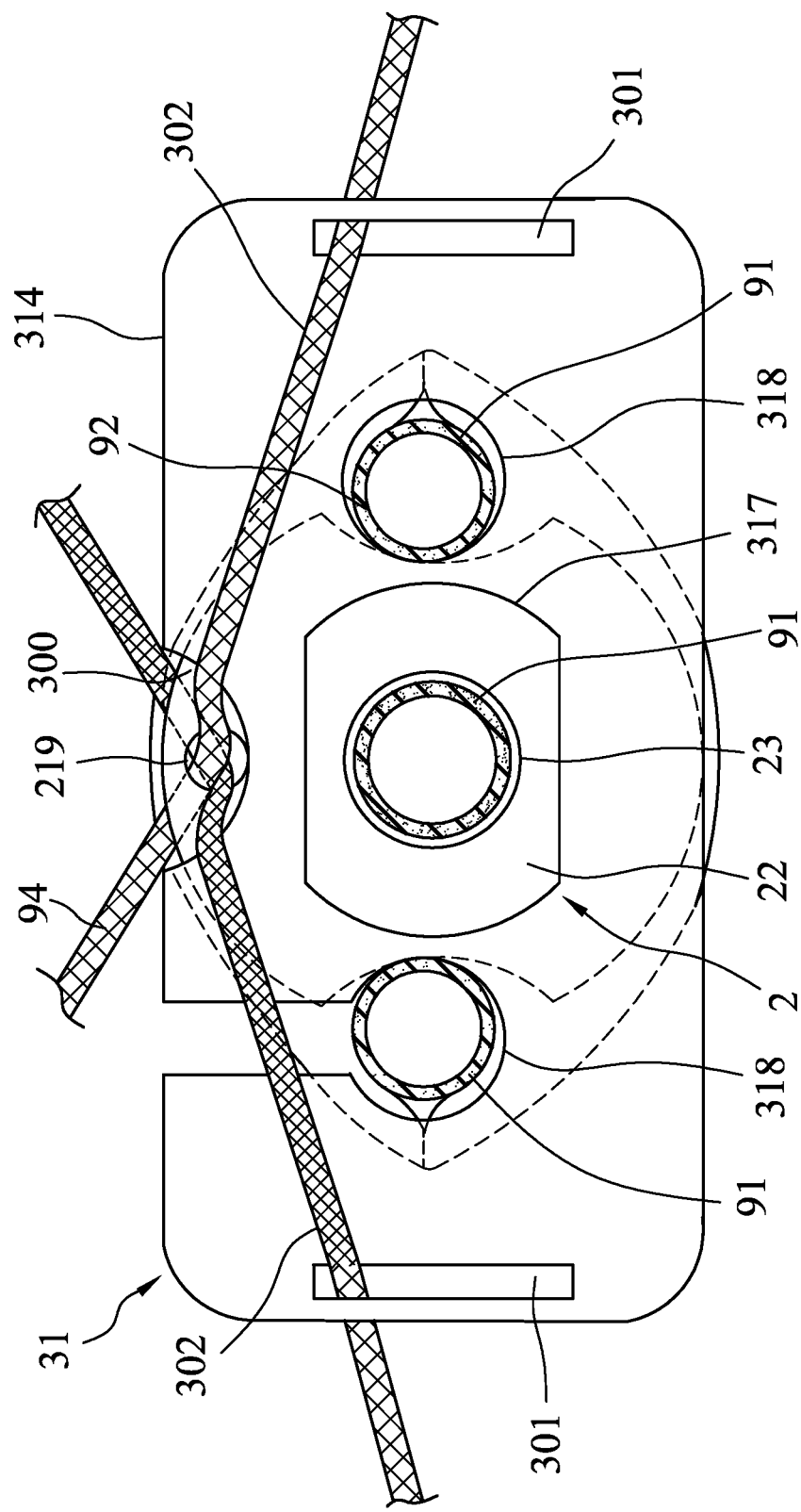
FIG. 9 is an assembled partial sectional view of the third embodiment in a state of use.

Referring to FIGS. 8 and 9, the third embodiment of the bite device of this disclosure is suitable for cooperating with a fixing member 94 which is to be fixed on the head (not shown) of the patient. The third embodiment is identical to the first embodiment, and differs in the structure of the abutment portion 21 of the bite member 2 and the fixing plate structure 31 of the auxiliary member 3.

In this embodiment, the abutment portion 21 further has an aperture 219 extending through the front and rear abutment surfaces 212, 217 thereof and located above the central hole 23. The aperture 219 has a width smaller than that of the central hole 23.

The fixing plate structure 31 of this embodiment further has a notch 300 formed in the fourth side surface 314 that interconnects the top ends of the first and second side surfaces 311, 312, two slots 301 extending through the first and second side surfaces 311, 312, and two indentations 302 extending inwardly from the second side surface 312 toward the first side surface 311. The notch 300 has a semicircular shape, is located above the main auxiliary hole 317, and corresponds in position to the aperture 219. Each slot 301 has a rectangular shape, and is located between one of the secondary auxiliary holes 318 and a corresponding one of the third side surfaces 313. Specifically, each slot 301 is proximate to the corresponding third side surface 313. Each indentation 302 is elongated, and extends between and communicates with the notch 300 and a corresponding one of the slots 301. The indentations 302 are located above the main and secondary auxiliary holes 317, 318.

The fixing member 94 is a string or a gauze strip.

In use, after the bite member 2 is placed in the mouth 92 of the patient and the auxiliary member 3 is sleeved on the sleeve portion 22 of the bite member 2, the fixing member 94 is folded into halves, and the two free ends thereof are inserted through the aperture 219 in the abutment portion 22, are passed through the notch 300 in the fixing plate structure 31, and are then separately guided by the indentations 302 so as to be inserted into the respective slots 301. After the free ends of the fixing member 94 extend out of the respective slots 301, they are tied at the back of the head of the patient. On the other hand, the folded portion of the fixing member 94 can be directly sleeved on the head of the patient, or can be cut and then tied at the back of the head of the patient. As such, the bite member 2 and the auxiliary member 3 can be stably connected to each other and can be secured to the head of the patient. Finally, the soft tubes 91 are inserted into the mouth 92 of the patient after correspondingly passing through the central hole 23 of the bite member 2 and the secondary auxiliary holes 318 of the auxiliary member 3. Since there are many ways to use the fixing member 94 to stably connect the bite member 2 and the auxiliary member 3, and can vary according to the habits of different users, a detailed description thereof is omitted herein for the sake of brevity.

Figure 10:
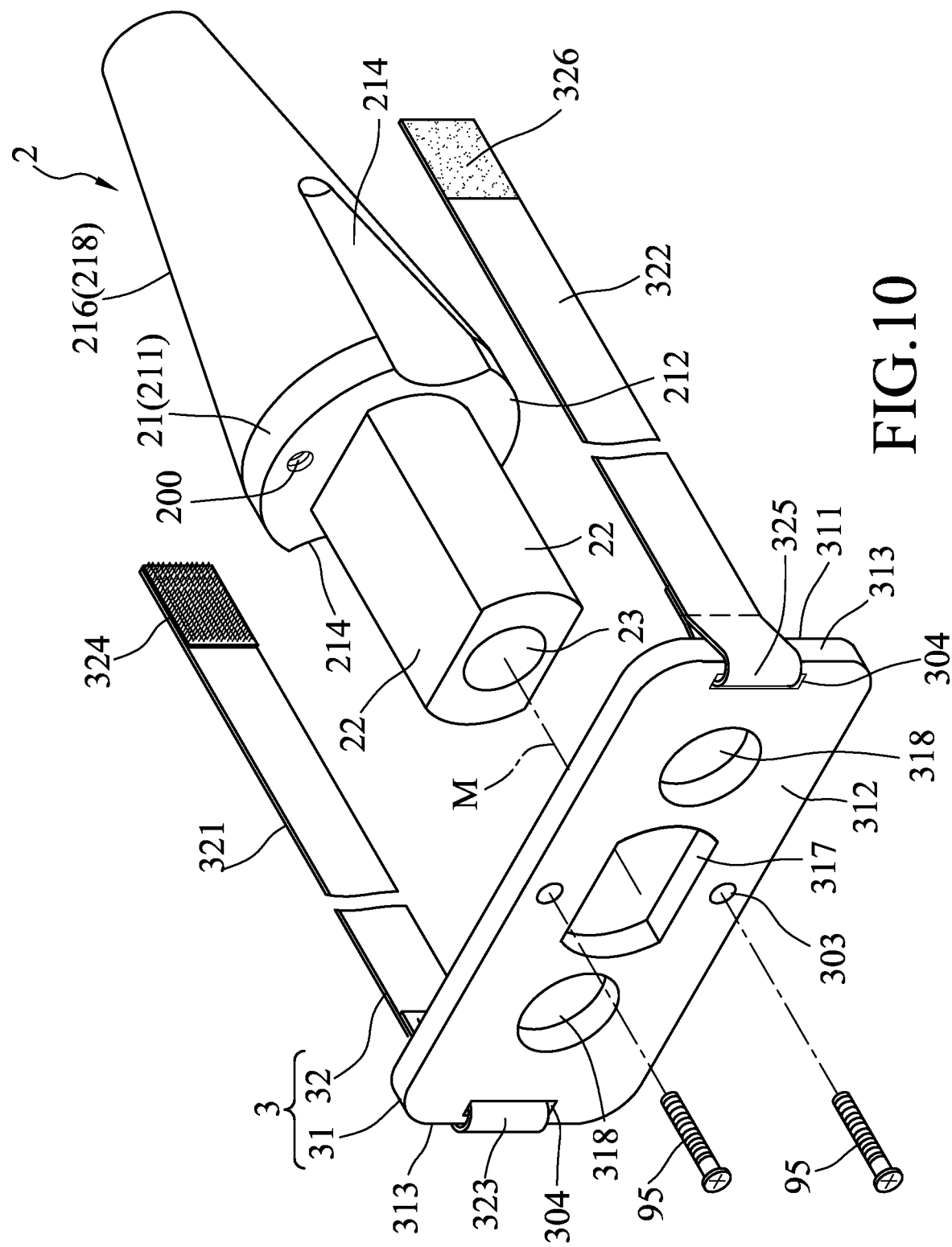
FIG. 10 is an exploded perspective view of a bite device according to the fourth embodiment of the present disclosure.
Figure 11:
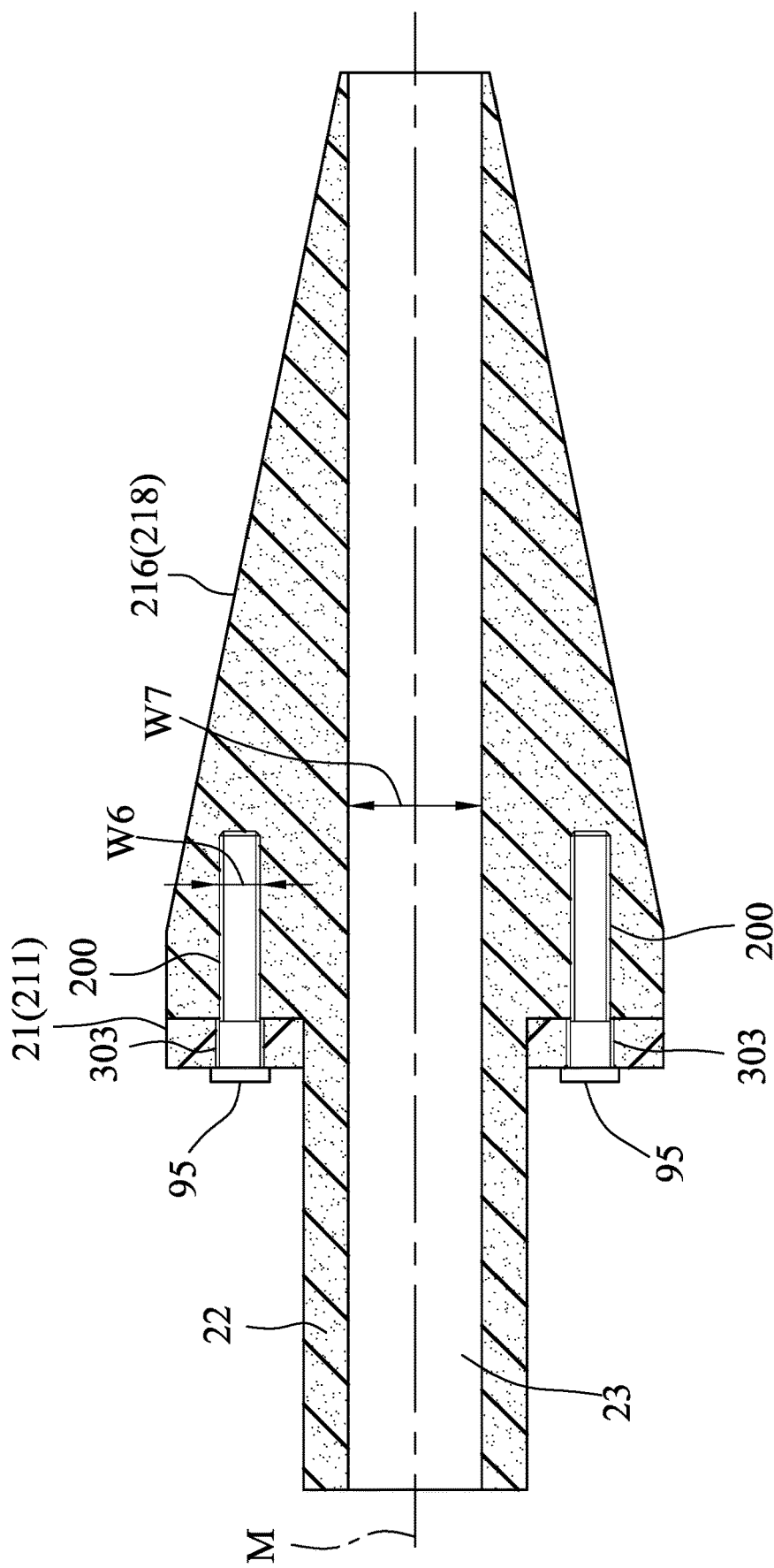
FIG. 11 is an assembled sectional view of the fourth embodiment.

Referring to FIGS. 10 and 11, the fourth embodiment of the bite device of this disclosure is suitable for cooperating with a plurality of fastening members 95. In this embodiment, two fastening members 95 are exemplified, and are configured as screws. The fourth embodiment is identical to the first embodiment, and differs in the structures of the bite member 2 and the auxiliary member 3.

In this embodiment, the bite member 2 is made of a silicone material and is molded in one piece. The biting portion 216 tapers rearwardly from a rear periphery of the outer peripheral surface 211 of the abutment portion 21. The cutouts 214 extend in a tapered manner from two opposite sides of the outer peripheral surface 211 toward two opposite sides of the outer peripheral surface 218 of the biting portion 216. The abutment portion 21 further has two spaced-apart first fixing holes 200 extending inwardly and rearwardly from the front abutment surface 212 and located on top and bottom sides of the central hole 23. Each first fixing hole 200 has a width (W6) smaller than a width (W7) of the central hole 23. In this embodiment, each first fixing hole 200 is a screw hole.

The fixing plate structure 31 of this embodiment does not have the passage 310 (see FIG. 3), but further has two spaced-apart second fixing holes 303 extending through the first and second side surfaces 311, 312 thereof and located on top and bottom sides of the main auxiliary hole 317, and two spaced-apart mounting holes 304 extending through the first and second side surfaces 311, 312 thereof. The second fixing holes 303 respectively correspond in position to the first fixing holes 200. Each mounting hole 304 is disposed between one of the secondary auxiliary holes 318 and a corresponding third side surface 313. Specifically, the mounting holes 304 respectively located in proximity to the third side surfaces 313.

In this embodiment, the auxiliary member 3 further includes a strap assembly 32. The strap assembly 32 includes a first strap 321 and a second strap 322 connected to the fixing plate structure 31. The first strap 321 includes a first fixed end 323 and a first connecting end 324 opposite to the first fixed end 323. The first fixed end 323 is inserted through a left one of the mounting holes 304, and is then folded back and sewn to itself so as to fix the first strap 321 to the left side of the fixing plate structure 31. The second strap 322 includes a second fixed end 325 and a second connecting end 326 opposite to the second fixed end 325. The second fixed end 325 is inserted through a right one of the mounting holes 304, and is then folded back and sewn to itself so as to fix the second strap 322 to the right side of the fixing plate structure 31.

In this embodiment, the first and second connecting ends 324, 326 are detachably connected to each other using a hook and loop fastening mechanism. Since there are many ways for connecting the first and second straps 321, 322 with the fixing plate structure 31 and the connecting ends 324, 326 of the straps 321, 322 to each other and are well known in the art, a detailed description thereof is omitted herein for the sake of brevity.

To use the bite device of this embodiment, the auxiliary member 3 is first sleeved on the sleeve portion 22 of the bite member 2 through the main auxiliary hole 317 thereof, after which the fastening members 95 are respectively inserted through the second fixing holes 303 to respectively engage with the first fixing holes 200, thereby fixing the fixing plate structure 31 to the bite member 2. Next, the biting portion 216 of the bite member 2 is placed in the mouth 92 (see FIG. 4) of the patient, and the first and second straps 321, 322 are connected to each other at the back of the head of the patient through the first and second connecting ends 324, 326. Finally, the soft tubes 91 (see FIG. 4) are inserted into the mouth 92 of the patient after correspondingly passing through the central hole 23 of the bite member 2 and the secondary auxiliary holes 318 of the auxiliary member 3.

It should be noted that the number of each of the first and second fixing holes 200, 303 may be one, three, etc., depending on actual requirements, and the number of the fastening member 95 is changed according to the number of each of the first and second fixing holes 200, 303.

In summary, the bite device of this disclosure utilizes the configurations of the fixing plate structure 31 of the auxiliary member 3 and the bite member 2, so that the soft tubes 91 inserted into the mouth 92 of the patient through the secondary auxiliary holes 318 can be limited by the fixing plate structure 31 and can be prevented from completely abutting against the lips 93 of the patient, thereby reducing the discomfort of the patient. Further, the soft tubes 91 inserted into the mouth 92 of the patient through the secondary auxiliary holes 318 can abut against the respective cutouts 214. Moreover, there is no need to use many gauze strips and breathable tapes for securing the soft tubes 91 in the mouth 92 of the patient, so that the efficiency of inserting the soft tubes 91 can be greatly improved. Therefore, the object of this disclosure can indeed be achieved.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A bite device comprising an auxiliary member and a bite member, the auxiliary member configured for removable connection with the bite member the bite member being configured to be placed in a mouth of a patient and being suitable for insertion of a plurality of soft tubes from an outside into the mouth of the patient, the bite member defining a centerline and including an abutment portion, a biting portion extending outwardly from one side of the abutment portion and configured to be located in the mouth of the patient, a sleeve portion extending outwardly from the other side of the abutment portion and opposite to the biting portion along the centerline, and a central hole that extends through the biting portion, the abutment portion and the sleeve portion and being suitable for insertion of one of the plurality of soft tubes therethrough, said auxiliary member comprising:

a fixing plate structure configured to be removably sleeved on the sleeve portion of the bite member and having a first side surface for facing the abutment portion of the bite member, a second side surface opposite to said first side surface, and a main auxiliary hole and at least one secondary auxiliary hole extending through said first side surface and said second side surface, said main auxiliary hole being configured to be sleeved on the sleeve portion of the bite member, said at least one secondary auxiliary hole being configured for insertion of another one of the plurality of soft tubes into the mouth of the patient;

wherein said fixing plate structure further has two third side surfaces interconnecting lateral ends of said first side surface and said second side surface, said at least one secondary auxiliary hole including two secondary auxiliary holes, each of said secondary auxiliary holes being located between said main auxiliary hole and a corresponding one of said third side surfaces, each of said secondary auxiliary holes not being blocked by the abutment portion of the bite member and being configured for insertion of a corresponding one of the plurality of soft tubes into the mouth of the patient; and wherein said fixing plate structure further has two fourth side surfaces, one of which interconnects top ends of said first side surface and said second side surface and top ends of said third side surfaces, and the other one of which interconnects bottom ends of said first side surface and said second side surface and bottom ends of said third side surfaces, said fixing plate structure further having a passage extending from said fourth side surface that interconnects said top ends of said first side surface and said second side surface to one of said secondary auxiliary holes, said one of said secondary auxiliary holes having a width larger than a width of said passage measured in a left-right direction transverse to the centerline, said passage being configured to allow the corresponding one of the plurality of soft tubes to pass therethrough and enter said one of said secondary auxiliary holes.

2. The bite device as claimed in claim 1, wherein the abutment portion of the bite member has an outer peripheral surface surrounding the centerline, and an abutment surface connected to a front periphery of the outer peripheral surface, and wherein said first side surface of said fixing plate structure has a flat area, and a plurality of spaced-apart raised areas protruding from said flat area and configured to face the abutment surface.

3. The bite device as claimed in claim 1, wherein:

said auxiliary member is suitable for cooperating with a fixing member which is to be sleeved on a head of the patient;

the abutment portion of the bite member has an outer peripheral surface surrounding the centerline, a front abutment surface connected to a front periphery of the outer peripheral surface, and a rear abutment surface opposite to the front abutment surface, the outer peripheral surface having two abutment areas spaced apart in a top-bottom direction transverse to the centerline, the sleeve portion extending outwardly from the front abutment surface, the biting portion extending outwardly from the rear abutment surface of the abutment portion and having a width measured in the top-bottom direction smaller than a width of the outer peripheral surface, the abutment portion further having an aperture extending through the front abutment surface and the rear abutment surface and configured for extension of free ends of the fixing member therethrough; and said fixing plate structure further has a notch formed in said fourth side surface that interconnects said top ends of said first side surface and said second side surface and configured to correspond in position to the aperture, and two slots extending through said first side surface and said second side surface, each of said slots being located between said one of said secondary auxiliary holes and said corresponding one of said third side surfaces, said notch being configured to allow the free ends of the fixing member that extend out of the aperture to pass therethrough and fix to said slots, respectively, so that the fixing member can fix said auxiliary member and the bite member to the head of the patient.

4. The bite device as claimed in claim 3, wherein said fixing plate structure further has two indentations extending inwardly from said second side surface toward said first side surface, and each of said indentations extends between and communicates with said notch and a corresponding one of said slots for guiding the free ends of the fixing member from said notch to the corresponding one of said slots.

5. The bite device as claimed in claim 1, wherein:

said auxiliary member is suitable for cooperating with at least one fastening member;

the abutment portion of the bite member has an outer peripheral surface surrounding the centerline, a front abutment surface connected to a front periphery of the outer peripheral surface, and at least one first fixing hole extending inwardly from the abutment surface and having a width smaller than a width of the central hole; and said fixing plate structure further has at least one second fixing hole that extends through said first side surface and said second side surface, that is configured to correspond in position to the at least one first fixing hole, and that is configured for extension of the at least one fastening member into the at least one first fixing hole after extending therethrough so as to prevent movement of said auxiliary member relative to the bite member.

6. The bite device as claimed in claim 1, further comprising a strap assembly connected to two opposite sides of said fixing plate structure that are proximate to said third side surfaces and configured to surround a head of the patient.

7. The bite device as claimed in claim 1, wherein said fixing plate structure is made of a silicone material and is molded in one piece.

* * * * *